US011471352B2

(12) United States Patent
Gustavson et al.

(10) Patent No.: US 11,471,352 B2
(45) Date of Patent: Oct. 18, 2022

(54) RELOCATABLE POWER TAP HAVING INTEGRATED CURRENT MONITOR

(71) Applicant: American IV Products, Inc., Harmans, MD (US)

(72) Inventors: Paul K. Gustavson, Gambrills, MD (US); Shannon Shingleton, Arnold, MD (US); Jeff Taltavull, Sykesville, MD (US); Tim Malkus, Severn, MD (US)

(73) Assignee: American IV Products, Inc., Harmans, MD (US)

( * ) Notice: Subject to any disclaimer, the term of this patent is extended or adjusted under 35 U.S.C. 154(b) by 242 days.

(21) Appl. No.: 16/878,204

(22) Filed: May 19, 2020

(65) Prior Publication Data

US 2021/0361506 A1   Nov. 25, 2021

(51) Int. Cl.
| | |
|---|---|
| *A61G 12/00* | (2006.01) |
| *H05B 45/30* | (2020.01) |
| *H01R 25/00* | (2006.01) |
| *H01R 13/66* | (2006.01) |
| *H01R 13/713* | (2006.01) |

(Continued)

(52) U.S. Cl.
CPC ....... *A61G 12/008* (2013.01); *H01R 13/6683* (2013.01); *H01R 13/713* (2013.01); *H01R 13/7175* (2013.01); *H01R 25/006* (2013.01); *H05B 45/30* (2020.01); *A61B 5/021* (2013.01); *A61B 5/02438* (2013.01); *A61B 5/08* (2013.01); *A61G 2203/20* (2013.01); *A61G 2203/78* (2013.01); *A61M 5/1415* (2013.01)

(58) Field of Classification Search
CPC ........ A61G 12/00; H05B 45/00; H01R 13/00; H01R 25/00; G01R 19/00
See application file for complete search history.

(56) References Cited

U.S. PATENT DOCUMENTS

| | | |
|---|---|---|
| 5,962,932 A | 10/1999 | Matlo |
| 7,324,006 B2 | 1/2008 | Godard |

(Continued)

OTHER PUBLICATIONS

Product Sheet for Leviton 53C6M-1N5 Power Strip, retrieved on May 19, 2020 at www.leviton.com.

(Continued)

*Primary Examiner* — Rexford N Barnie
*Assistant Examiner* — Joseph N Inge
(74) *Attorney, Agent, or Firm* — Womble Bond Dickinson (US) LLP

(57) ABSTRACT

A medical electrical equipment power tap has multiple sockets and a power cord with a maximum current rating. The power tap includes a display to indicate information related to an instantaneous current draw of the power tap. The power tap also includes an electrical circuit which determines whether the instantaneous current draw exceeds a predetermined maximum allowed current which is less than the maximum current rating. The display provides a visual indication when the power tap's current draw exceeds the maximum allowed value, signifying that at least one item of medical electrical equipment should be unplugged from the power tap. The electrical circuit includes a current loop which passes through a structural portion of the power tap's housing for independently gauging the instantaneous current draw using a clamp probe.

21 Claims, 11 Drawing Sheets

(51) Int. Cl.
  *H01R 13/717* (2006.01)
  *A61B 5/021* (2006.01)
  *A61B 5/024* (2006.01)
  *A61B 5/08* (2006.01)
  *A61M 5/14* (2006.01)

(56) References Cited

U.S. PATENT DOCUMENTS

| | | |
|---|---|---|
| 7,777,995 B2 | 8/2010 | Malkus et al. |
| 8,221,154 B1 | 7/2012 | Paquette |
| 8,415,828 B2 | 4/2013 | Johnson, Jr. et al. |
| 8,558,710 B1 | 10/2013 | Nitz |
| 9,316,672 B2 | 4/2016 | Soneda et al. |
| 9,543,692 B2 | 1/2017 | Shomali |
| 2009/0046402 A1* | 2/2009 | Malkus ............. H01R 25/003 361/87 |
| 2011/0012589 A1* | 1/2011 | Greenberg ............ G01R 15/186 324/127 |
| 2012/0001768 A1* | 1/2012 | Radosavljevic ......... H04Q 9/00 340/870.03 |
| 2015/0118896 A1* | 4/2015 | Shomali ............. H01R 13/5224 439/540.1 |
| 2015/0309825 A1* | 10/2015 | Farkas ................. G06F 9/5011 718/1 |
| 2020/0309825 A1* | 10/2020 | Arredondo ....... G01R 19/16547 |

OTHER PUBLICATIONS

Product Sheet for Leviton 53C6M-1N7 Power Strip, retrieved on May 19, 2020 at www.leviton.com.
Product Sheet for Leviton 53C6M-2N7 Power Strip, retrieved on May 19, 2020 at www.leviton.com.

* cited by examiner

RELOCATABLE POWER TAP HAVING INTEGRATED CURRENT MONITOR

BACKGROUND OF THE INVENTION

Field of the Invention

The present invention concerns a special purpose relocatable power tap (SPRPT) suitable for powering medical electrical equipment of the sort found in a hospital room, such as in an intensive care unit (ICU). More particularly, it concerns a relocatable power tap which indicates when the total current draw due to multiple items of medical electrical equipment being plugged in, reaches a predetermined threshold which is less than the maximum current rating for that power tap. Such power tap can be mounted on an IV pole of the sort used for hanging intravenous fluids, on the leg, rail or flat side of a medical cart configured to carry such medical monitoring equipment, and even on a leg or rail of a hospital bed.

Background

There are many industry standards governing medical electrical equipment, such as IV pumps, patient monitors, and the like, that are used in medical and clinical settings.

Certain industry standards require that the current draw from a special-purpose relocatable power tap (SPRPT) be no greater than a predetermined percentage of the maximum current draw for which the connecting cordage of the power tap is rated. Thus, if the connecting cordage of the power tap is rated for a maximum current draw of 16 Amps and the predetermined percentage is 75%, a user of the power tap (e.g., a medical professional such as a nurse or doctor) should unplug one of the medical electrical equipment devices from the power tap if 12 Amps are already being drawn. Similarly, if the connecting cordage of the power tap is rated for a maximum current draw of 20 Amps and the predetermined percentage is again 75%, the user should unplug one of the medical electrical equipment devices from the power tap if 15 Amps are already being drawn.

Oftentimes, such items of medical electrical equipment are mounted on an Intravenous (IV) pole, which typically is supported by wheeled legs, to facilitate positioning and transport. U.S. Pat. Nos. 7,777,995 and 9,543,692, whose contents are incorporated by reference in their entirely, exemplify pole-mountable relocatable power taps whose back sides are configured to be mounted on such an IV pole.

SUMMARY OF THE INVENTION

In one aspect, the subject matter of the present application is directed to a medical electrical equipment relocatable power tap having a power cord with a maximum current rating. The relocatable power tap includes a housing having a front side, a rear side, a top side and a bottom side, which together define a housing interior. At least four electrical sockets are provided on the front side of the housing, each electrical socket configured to receive a plug belonging to an item of medical electrical equipment. An electrical circuit mounted in the housing interior is configured to measure an amount of electrical current being drawn by the power tap. A display provided on the front side of the housing and driven by the electrical circuit is configured to provide information reflective of whether the amount of electrical current being drawn by the power tap after an additional item of medical electrical equipment has been plugged into an unoccupied one of the plurality of electrical sockets of the power tap exceeds a maximum allowed current which is less than the maximum current rating of the power cord.

DETAILED DESCRIPTION OF THE INVENTION

The industry standards, NFPA-99 (National Fire Protection Association Health Care Facilities Code Handbook) and UL1363/1363A (Underwriters Laboratories Standard for Relocatable Power Taps) are incorporated by reference to the extent necessary to understand the present invention. It is understood that these industry standards may change from time to time. One aspect of these industry standards that is particularly relevant to the present invention is that a medical equipment grade power tap should not be operated at its maximum current rating, but instead be limited a current draw lower than its maximum current rating (a "maximum allowed current").

Figures 1, 15:
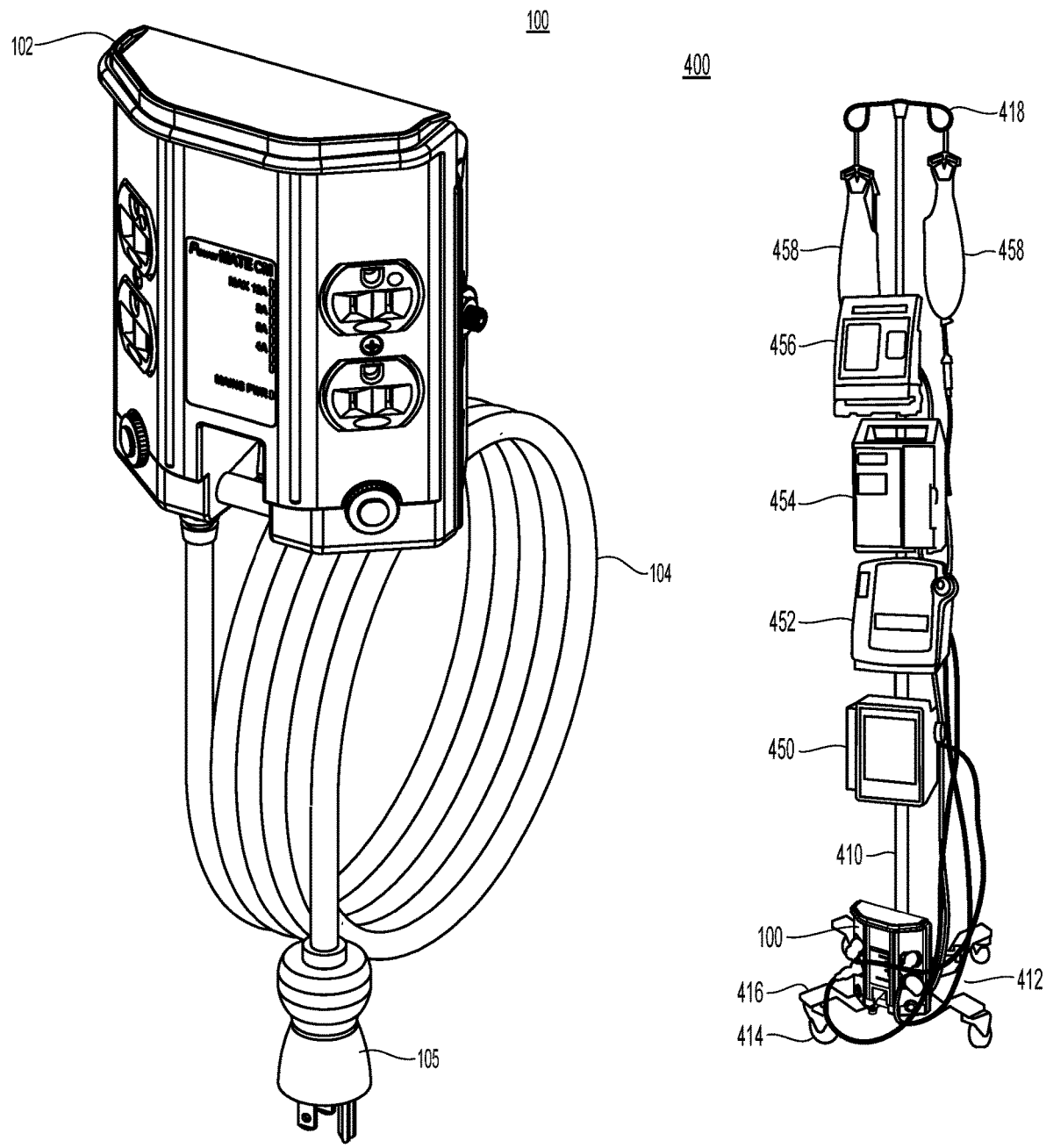
FIG. 1 shows a special purpose relocatable power tap (SPRPT) in accordance with the subject matter of the present application.
FIG. 15 shows an SPRPT mounted on an IV pole.

FIG. 1 shows an isometric view of an exemplary special purpose relocatable power tap (SPRPT) 100 in accordance with one embodiment of the subject matter of the present application. The SPRT 100 includes a housing 102 to which a power cord 104 having a plug 105 is connected. In one embodiment, the power cord is 16 AWG and between 10-20 feet long.

Figure 2:
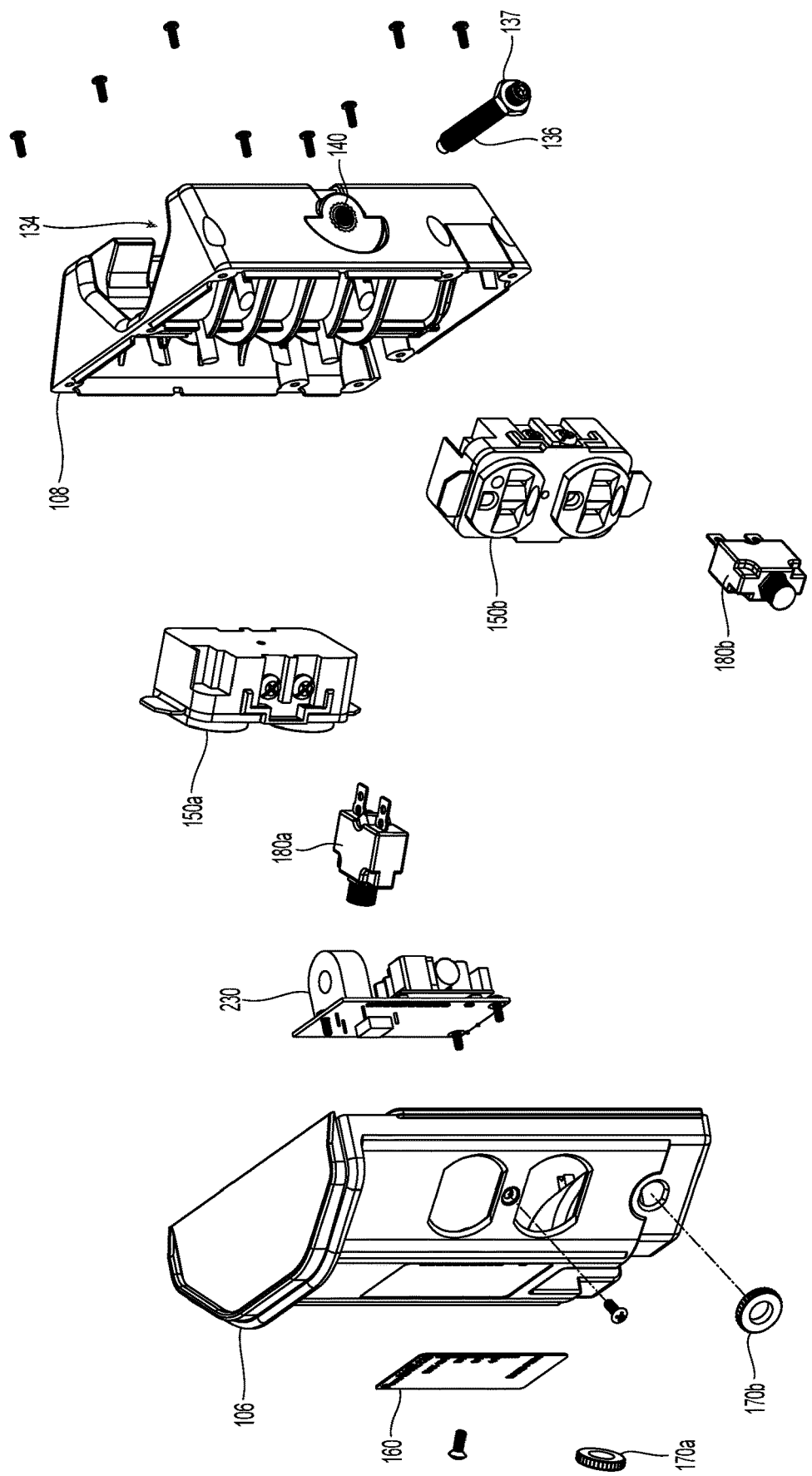
FIG. 2 shows an exploded view of the relocatable power tap.

As seen in the exploded view of FIG. 2, the housing 102 includes a front housing 106 and a rear housing 108. The housing 102 supports a plurality of dual receptacles 150a, 150b, each comprising a pair of sockets 154a, 154b, 150c, 150d suitable for receiving plugs from medical electrical equipment. In a preferred embodiment, the dual receptacles 150a, 150b are hospital grade receptacles.

The housing 102 also supports a printed circuit board assembly 230 (PCBA), a display 160, and first and second breaker circuits 180a, 180b which are secured to the housing 102 via respective breaker mounting nuts 170a, 170b.

The power cord 104 enters the housing 102 via the rear housing 108 and supplies power from a wall or floor outlet to the receptacles 150a, 150b, the PCBA 230 and the display 160, as discussed further below.

Figure 5:
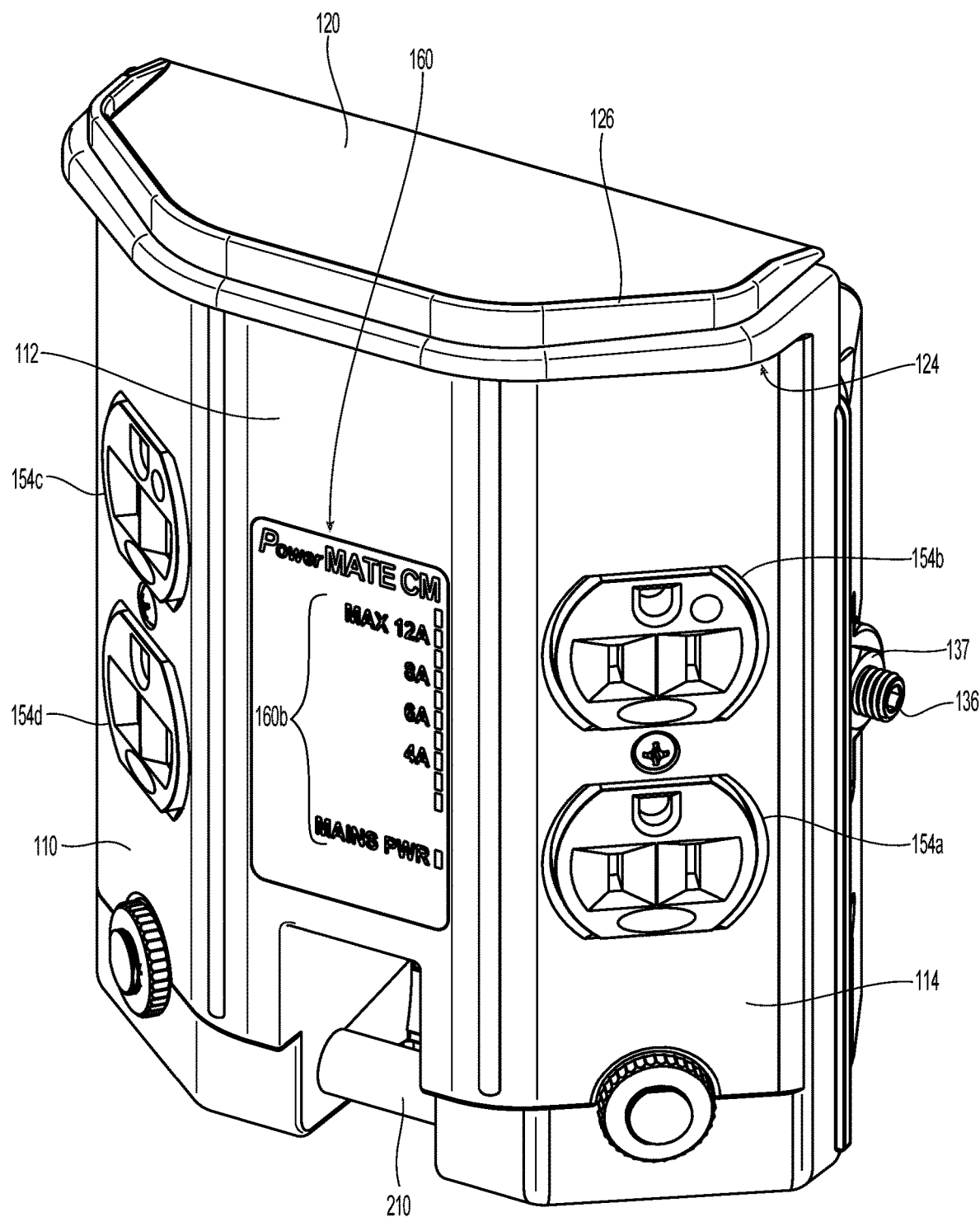
FIG. 5 shows an isometric view of the power tap housing.
Figure 6:
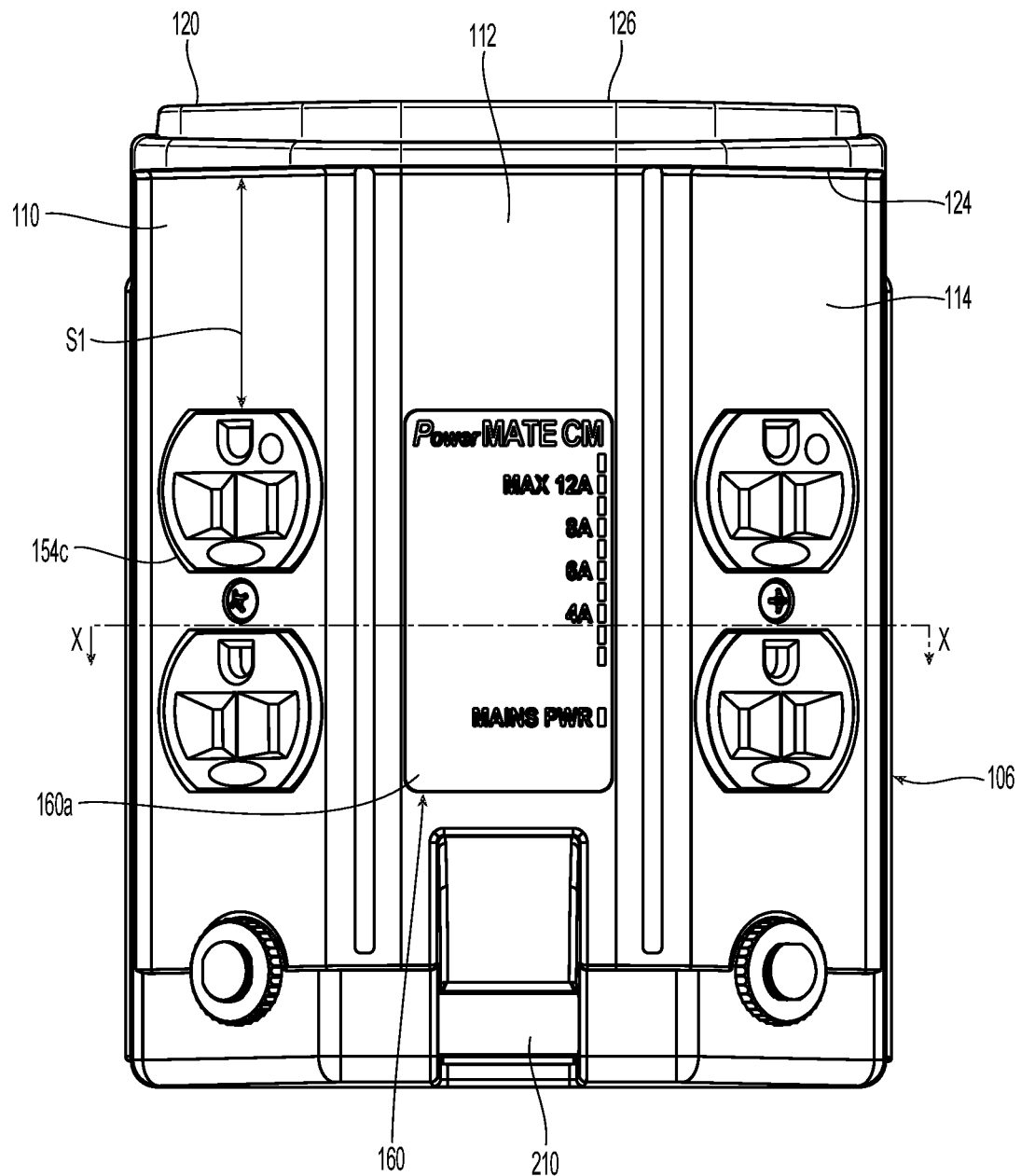
FIG. 6 shows a front view of the power tap housing.

As seen in FIGS. 5-6, the front housing 102 includes a front housing top 120 and front housing bottom 122. Extending between the front housing top 120 and front housing bottom 122, the front housing 102 has a first facet 110, a second 112 and a third facet 114, with the second facet 112 located between the first facet 110 and the third facet 114. The dual receptacles 150a, 150b are located in the first facet 110 and the third facet 114, respectively, while the display 160 is located in the second facet 112. The three facets are generally planar and face in different directions. The housing components may be molded from a resin or other suitable material, or they may be made by additive manufacturing ("3-D printed").

Proximate the front housing top 120, the front housing 102 has a top overhang 124 which projects beyond ("overhangs") the facets 110, 112, 114. Rising from the front housing top 120 along the overhang is a top lip 126. The top overhang 124 and the top lip 126 help prevent liquids spilled onto the housing top 120 (from, e.g., an IV bag mounted above the SPRPT) from dribbling down the facets onto the display 160 or the receptacles 150a, 150b.

On the first and third facets, the top overhang 124 is spaced apart by a minimum distance S1 from the receptacles 150a, 150b. In some embodiments, the minimum spacing S1 is at least 5 cm.

As seen in FIGS. 7-10, the rear housing 108 has a rear housing top 130 and a rear housing bottom 132. Along its back side, the rear housing 108 is provided with a longitudinal mounting scheme suitable for mounting the SPRPT 100 to a pole. Within the meaning of the present invention, a "pole" is a structural member having a longitudinal extent, and a cross-section, such as the circular cross-section of a pole member of an IV pole, the square cross-section of a leg or rail of a medical cart or a leg or rail of a hospital bed. Poles may also have other cross-sectional shapes, such as rectangular and triangular, among others. In the present application, the term "pole-mountable" is intended to cover mounting assemblies that can be removably attached to poles of a variety of cross-sections. The mounting scheme comprises a rear channel 134 into which such a pole is at least partially received. In one embodiment, the rear channel 134 is configured to be able to mount the SPRPT 100 to a pole having a thickness, such as a diameter, of up to 2.5 inches, or roughly 6.5 cm. While the rear channel 134 is shown in the figures to be vertically oriented for mounting the SPRTP 100 on a vertically directed pole, in other embodiments (not shows), the rear channel may be horizontally oriented to facilitate mounting the SPRTP 100 onto a horizontally extending rail of a medical cart or hospital bed.

Figure 7:
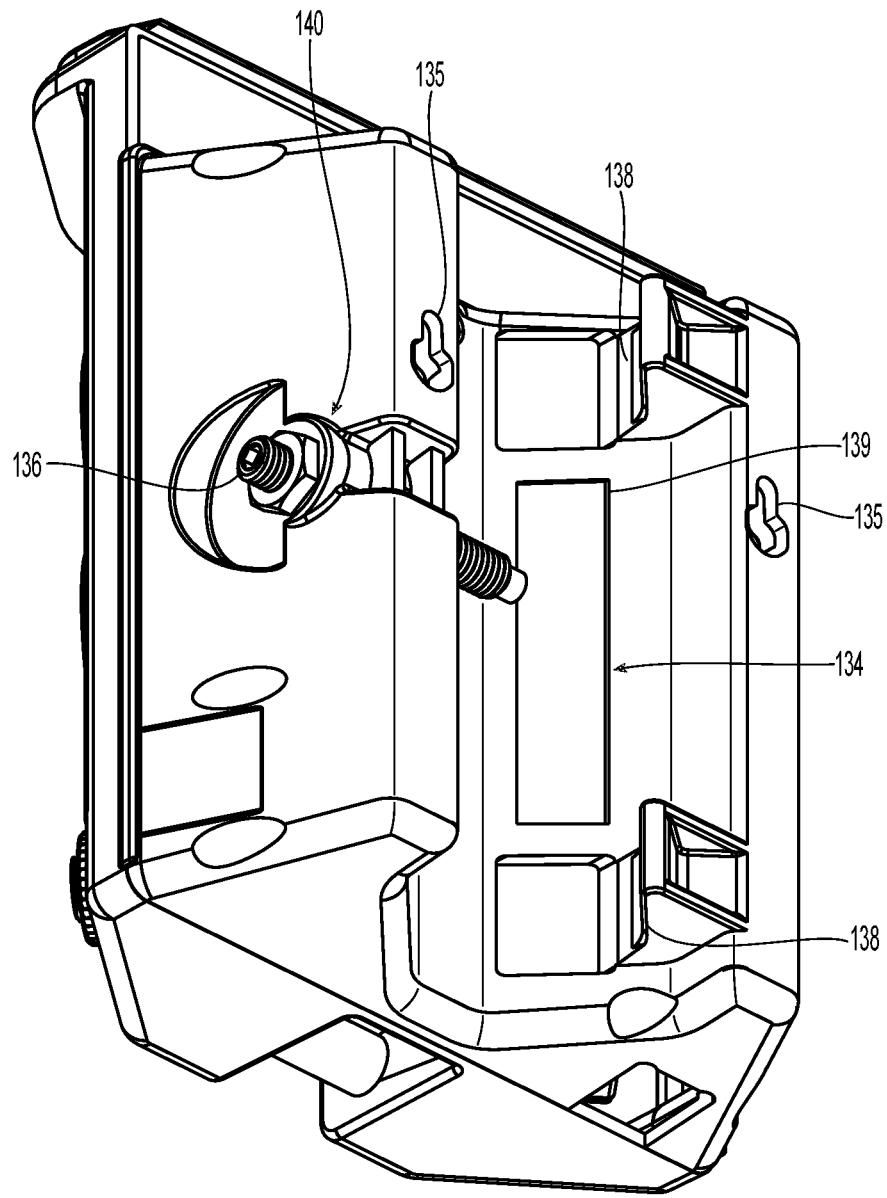
FIG. 7 shows an isometric rear view of the power tap housing.
Figure 8:
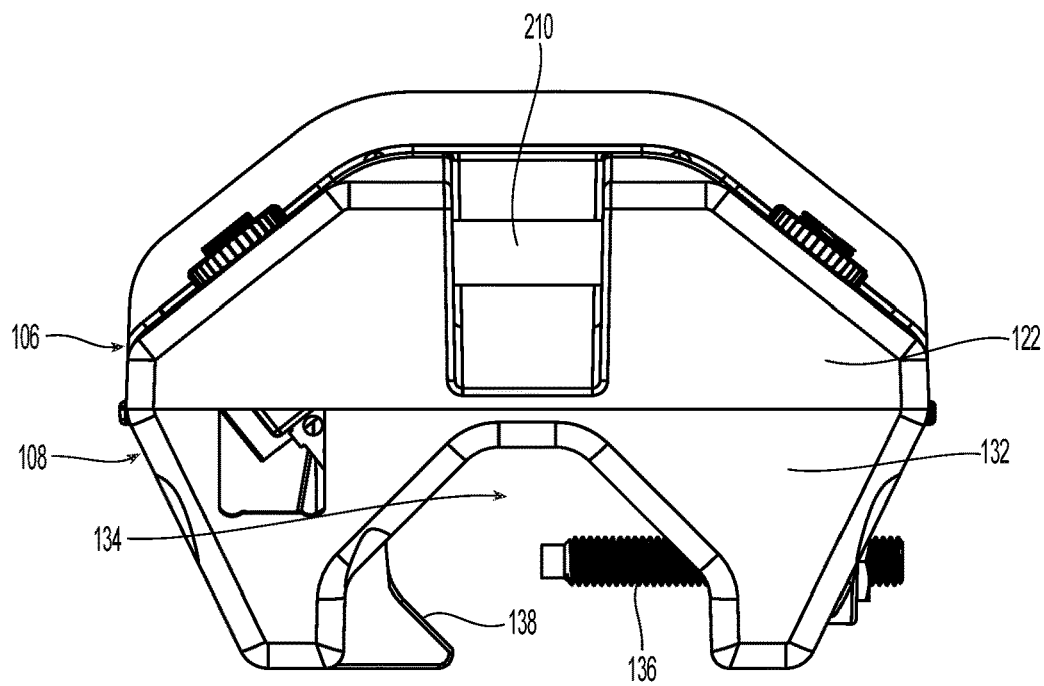
FIG. 8 shows a bottom view of the power tap housing.
Figure 9:
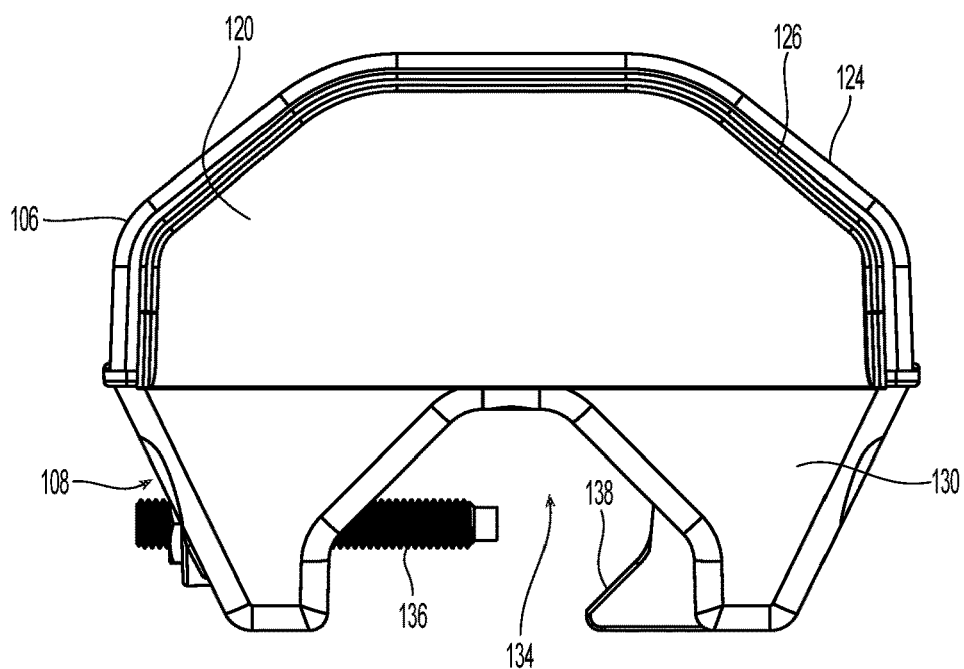
FIG. 9 shows a top view of the power tap housing.

As seen in FIG. 7, the rear housing 108 may further be provided with two spaced apart mounting apertures 135. In the embodiment shown, the mounting apertures 135 are located on opposite sides of the rear channel 134. The mounting apertures 135 are configured to receive fasteners (e.g., screws, bolts, rivets, prongs, etc.) for mounting the SPRPT to a surface, such as the side of a medical cart. In some embodiments, such mounting apertures may be provided in flanges or other structures connected to the housing. And in embodiments in which the SPRPT is not configured to be pole-mounted (e.g. lacks a rear channel 134), the mounting apertures may be the only structures provided for mounting the SPRPT.

A clamping set-screw 136 is provided to secure the SPRPT 100 to a pole, in cooperation with a pair of spaced-apart clamping surfaces 138 formed on the rear housing 108. The clamping set-screw 136 terminates in an abutment cap 142. The clamping set-screw 136 passes through a threaded aperture 140 formed in a first exterior wall of the rear housing 108, and is locked in place by the user with an anti-removal locking nut 137. The clamping set-screw 136 extends in a first direction transverse to the channel 134. The abutment cap 142 is capable of abutting a pole on one side. Meanwhile, the spaced-apart clamping surfaces 138, which face in a second direction opposite the first direction, are capable of abutting a pole from the opposite side, when the SPRPT 100 is positioned such that a portion of a pole is received into the channel.

Thus, the clamping set-screw 136 and the pair of clamping surfaces 138 are capable of frictionally mounting the housing to a pole, when the SPRPT 100 is positioned such that a portion of a pole is received into the channel 134. One or more friction-enhancing pads 139 may be provided on a wall of the channel 134 to retard slippage of the SPRPT relative to the pole.

FIG. 15 shows the SPRPT 100 being used in conjunction with an IV pole 400. The IV pole 400 comprises a base 412, a longitudinally extending pole member 410 and terminates at the top end in one or more hooks 418 for suspending IV bags. The base has a plurality of legs 416 provided with casters 414, to facilitate transport of the IV pole 400. The SPRPT 100 is mounted on the longitudinally extending pole member 410, proximate the base 412 of the IV pole 400. As also seen in FIG. 15, assorted medical electrical equipment may be mounted on the longitudinally extending pole member 410 and plugged into the power supply. Thus, medical electrical equipment such as a breathing monitor 450, a blood pressure monitor 452, a heart monitor 454 and an IV pump 456, may be accommodated, along with one or more IV bags 458 suspended from the hooks 418. Each piece of equipment 450, 452, 454, 456 may be connected to a single patient, and is plugged into the SPRPT 100.

The total load current supplied through the SPRPT 100 to these plugged-in medical electrical devices must not exceed any applicable maximum load current industry standard, such as the pertinent industry standard set forth by NFPA-99, UL1363/1363A. Currently, the industry standard for maximum allowable load current passing through SPRPT 100 in NFPA-99 is no more than 75% of the ampacity ("maximum current rating") of the connecting power cord 104. This 75% value is a predetermined percentage of the maximum current rating, and results in a "maximum allowed current" which is less than the maximum current rating. A user may determine whether the instantaneous current of the SPRPT 100 complies with the maximum allowed current by observing a display 160.

Figure 3:
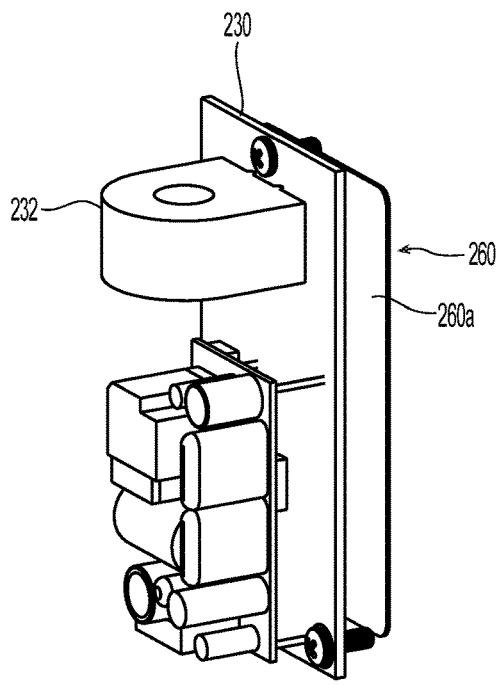
FIG. 3 shows an isometric view of the PC Board carrying the electrical circuit.
Figure 4:
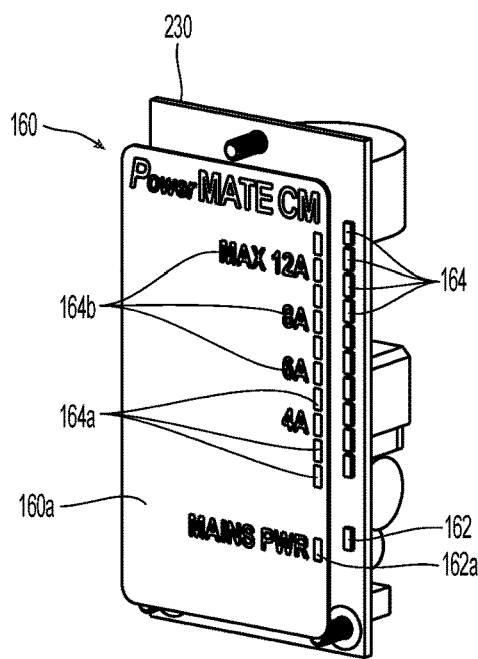
FIG. 4 shows an isometric view of the display panel.

In the embodiment seen in FIGS. 3-4, the display 160 comprises a display panel 160A overlying a plurality of indicator lights 162, 164 mounted on one side of the PCBA 230 which, in turn, is mounted to the inside of the front housing 106. Openings in the front housing 106, and more particularly in the second panel 112, allow the indicator lights 162 164 to be viewed.

In one embodiment, the indicator lights are light emitting diodes (LEDs). To view the indicator lights 162, 164, the display panel 160 is provided with windows 162a, 164a which align with the indicator lights 162, 164. The windows 162a, 164b may be transparent and/or translucent, and may be colored. Amperage indicia 160b may be provided on the display panel 160a adjacent the windows 162a, 164a to inform a user of the significance of the corresponding indicator lights.

Indicator light 162 may be a mains indictor light configured to indicate that the SPRPT 100 is plugged in. Indicator light 162 can be viewed through a mains display window 162*a*.

Indicator lights 164 may comprise a plurality of current indicator lights arranged in a row, (in this embodiment, a vertical row), and each of the indicator lights 164 main be viewed through a corresponding current display window 164*a*. Taken together, the current indicator lights 164 provide an indication of current draw of the SPRPT 100. For instance, the number of current indicator lights 164 that are lit up at any given instant may be roughly proportional to the instantaneous current draw of the SPRPT.

Example 1

An SPRPT having a power cord with a maximum current rating of 16 Amps is provided with a total of 10 current indicator lights 164 arranged in a vertical row and configured to function as a bar graph. The topmost indicator light is colored red while the remaining lights below in the vertical row are colored green. The display panel 160 is provided with a corresponding number of vertically arranged windows 164*a* aligned with the indicator lights 164. Of the 16 Amps, no more than 75%, or 12 Amps, is the maximum allowed current (under the Standard) that can be drawn by all medical electrical equipment plugged into that SPRPT 100. As items of medical electrical equipment are incrementally plugged in to the SPRPT, additional green indicator lights 164 closest to the bottom of the vertical row are turned on, reflecting the additional current draw. The dynamic range of the vertical row of indicator lights 164 is configured such that upon reaching a current draw of 12 Amps, the topmost (red) indicator light 164 of the vertical row is turned on. This informs the user that that the maximum allowed current has been exceeded and that the user must unplug at least one item of medical electrical equipment.

While in the disclosed embodiment, the display 160 comprises LEDs, in other embodiments the display may be a liquid crystal display (LCD) or other screen driven by a processor, ASIC or other suitable device. Also, in some embodiments, in addition to a visual display indicating when the maximum allowed current is exceeded, the SPRPT may be configured to emit an audible signal (e.g., a tone) to inform an operator that the maximum allowable current has been exceeded.

Figure 4A:
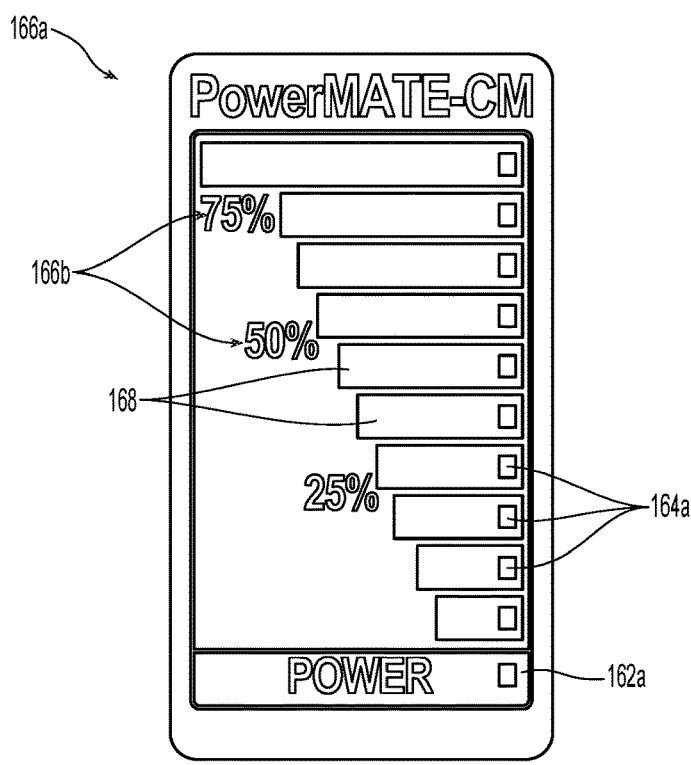
FIG. 4A shows an alternate embodiment of a display panel.

FIG. 4A shows an alternate embodiment of a display panel 166*a* which includes windows 162, 164*a* much like display panel 160*a*. Display panel 166*a* includes percentage indicia 166*b* (25%, 50%, 75%) which inform the user what percentage of the power cord's maximum current rating is being utilized at any given instant. Additional indicia may include a horizontally oriented indicator bar 168 associated with each current display window 164*a*. Each indicator bar 168 has a different length, the length of a given indicator bar 168 being proportional to the SPRPT's current draw when its corresponding indicator light 164 is illuminated. Much like display panel 160*a*, as items of medical electrical equipment are incrementally plugged in to the SPRPT 100, additional green indicator lights 164 closest to the bottom of the vertical row are turned on, reflecting increased current draw. When the current draw exceeds the maximum allowed current, the topmost (red) indicator light 164 in the vertical row of lights is turned on, in addition to all the green indicator lights below. This informs the user that that the maximum allowed current has been exceeded and that the user must unplug at least one item of electrical medical equipment.

In a variation of the display 160, only one of the ten lights is on at any given time. Thus, as additional items of electrical medical equipment are plugged into the SPRPT 100, a different (higher) one of the green indicator lights 164 is illuminated. And when the SPRPT's current draw exceeds the maximum allowed, only the topmost (red) indicator light is on, and none of the green lights below are on. Such a variation may be used with either display panel 160*a* or 166*a*.

Figure 10:
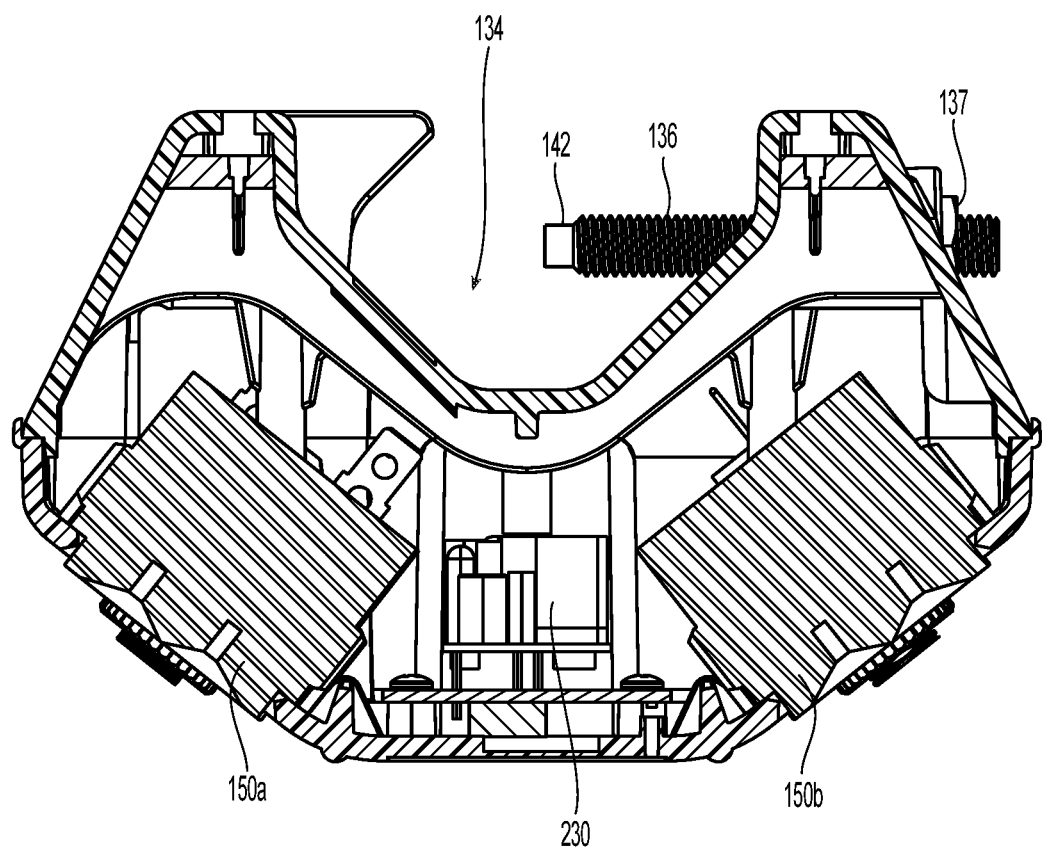
FIG. 10 shows a cross-sectional view taken along lines X-X of FIG. 6.
Figure 11:
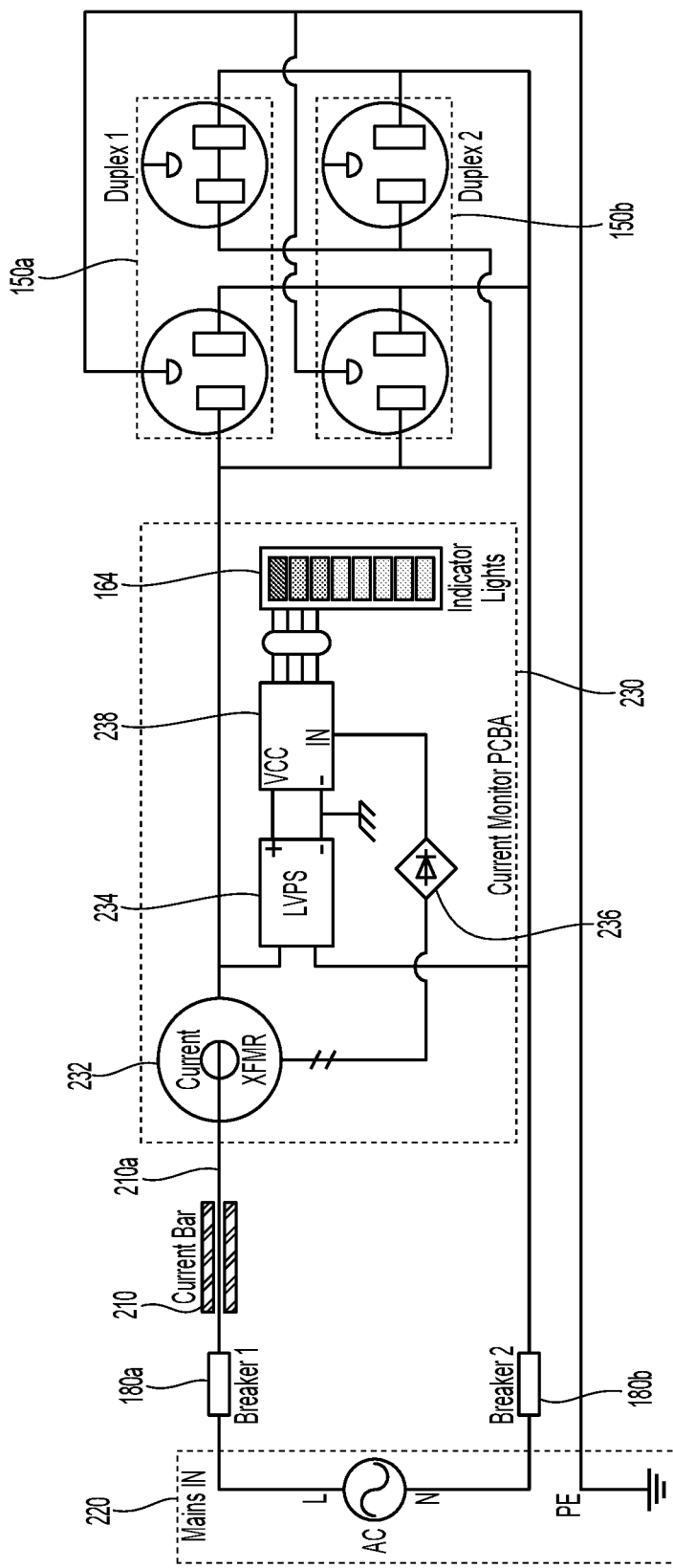
FIG. 11 shows the protection circuit layout.

As depicted in FIG. 10, The SPRPT's plug 105 is connected to electrical mains 220 to supply power to the SPRTP 100. The pair of circuit breakers 180*a*, 180*b* is in series with the plug 105, and are configured to protect the SPRPT 100 from excess current draw. The circuit breakers 180*a*, 180*b* are also connected in series with the first and second dual receptacles 150*a* and 150*b*, and the PCBA 230, thereby supplying power thereto.

On a first side thereof, the PCBA 230 carries a current transformer 232, a medical-rated, switch mode low voltage power supply 234 (LVPS) which includes a full wave rectifier 234 and a display circuit 238 configured to drive the current indicator lights 164. As seen in the FIGS. 3 and 4, the current indicator lights 164 may be mounted on a second side of the PCBA 230, opposite the first side.

The LVPS 234 supplies DC power to various circuit components attached to the board. The LCPS 234 also powers the above-described indictor lights 162, 164.

Figure 12:
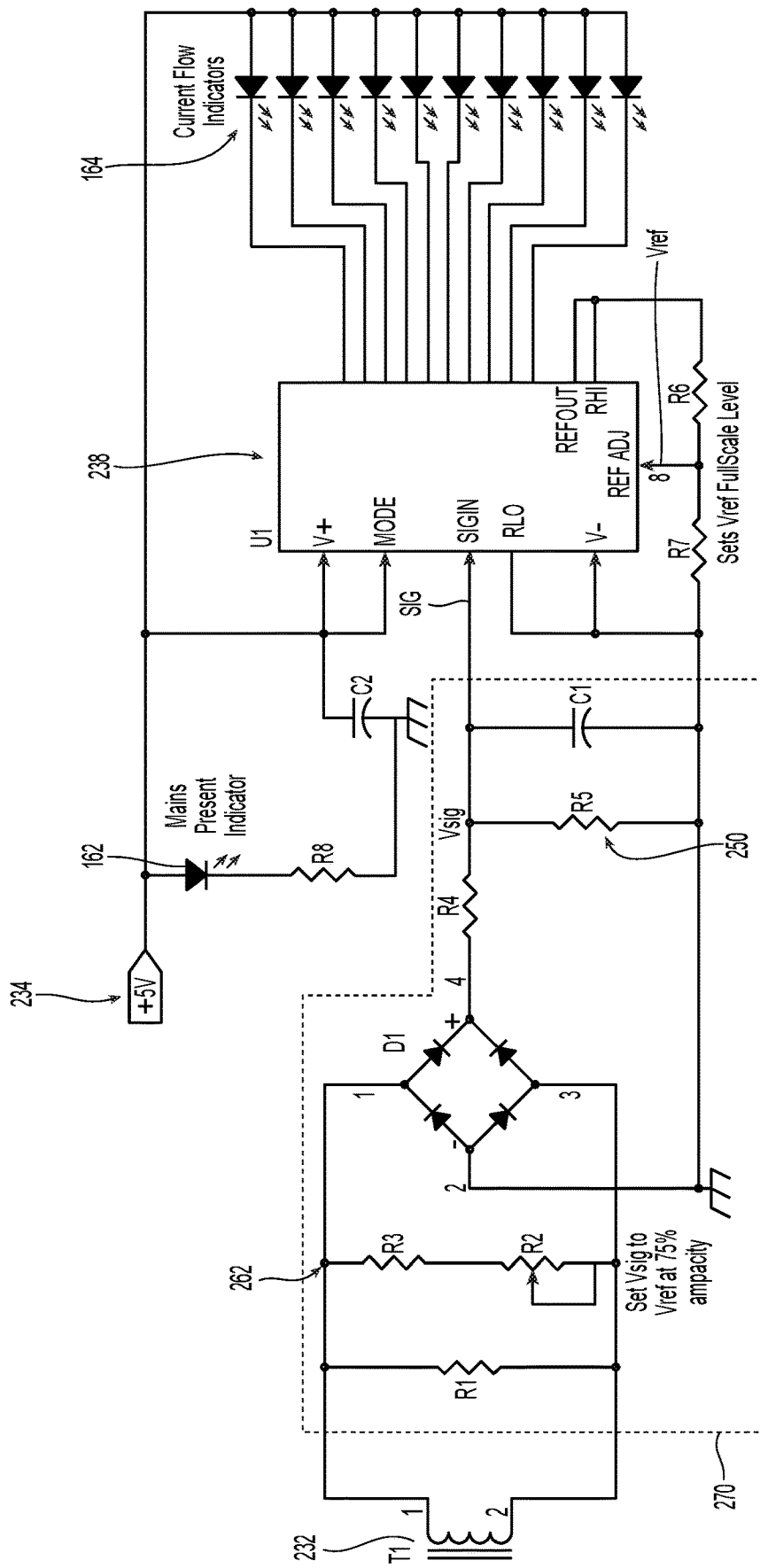
FIG. 12 shows the overall electrical circuit.

With reference to the circuit seen in FIG. 12, current draw through the "hot" leg of the mains input of the SPRPT 100 is detected by transformer T1 232 which serves as a current sensor.

The resistor network containing resistors R1/R2/R3 presents an adjustable load on T1, with resistor R2 configured as a potentiometer. The output of the transformer/resistor network is rectified by the full-bridge rectifier 236 which is implemented as an integrated circuit D1. Resistors R2 and R3 function as a voltage divider 262 which adjusts the transformer T1 load. Adjusting the transformer load by turning potentiometer R2 sets the network output waveform to the desired level. A filter network 250 containing resistors R4 and R5 and capacitor C1 cleans up the output by removing any residual ripple from the waveform. The cleaned DC output serves as a drive signal SIG having a voltage level of Vsig. As such, resistors R1, R2, R3, integrated circuit rectifier D1, and the filter network 250 which includes resistors R4, R5 and capacitor C1 collectively function as a detection circuit 270 configured to measure the instantaneous electrical current sensed by the transformer T1, and output a drive signal SIG in response thereto. A voltage level Vsig of the drive signal SIG is proportional to the instantaneous electrical current.

Drive signal SIG is input to the display circuit 238. In one embodiment, the display circuit 238 is implemented by a display driver integrated circuit U1, and more specifically, an LM3914 Dot/Bar Display Driver IC, available from Texas Instruments®. The LM3914 senses analog input voltage levels and can be configured to drive 10 LEDs via 10 output pins, providing a linear analog display. One or more comparators internal to the LM3914 are used to compare the input voltage with a reference voltage to determine which all of the ten outputs are enabled.

The reference voltage Vref is the full-scale voltage level for the LEDs 164 driven by display circuit 238. Vref is determined by resistors R6 and R7 which form a voltage divider. Vref is set such that the one red LED, meant to indicate excessive current draw, will be illuminated when the input exceeds the reference level Vref, thereby signifying that SPRPT 100 is drawing in excess of the maximum allowed current.

It can be seen from the foregoing that while Vref is a fixed voltage establishing the full-scale voltage range for the 10 output LEDs, Vsig is the rectified/filtered voltage output from the current transformer which forms the drive signal SIG to the display circuit 238. Moreover, the ratio of Vsig/Vref determines how many LEDS are turned on. If the ratio is one, then the topmost (red) LED is the vertical row is turned on. The remaining nine green LEDs indicate current flow below the maximum allowed level.

Power for the circuit seen in FIG. 12 is provided by the aforementioned LVPS 234. A single LED 162 connected to the output of the switch mode power supply indicates that mains voltage is present within the SPRPT 100.

Figure 14:
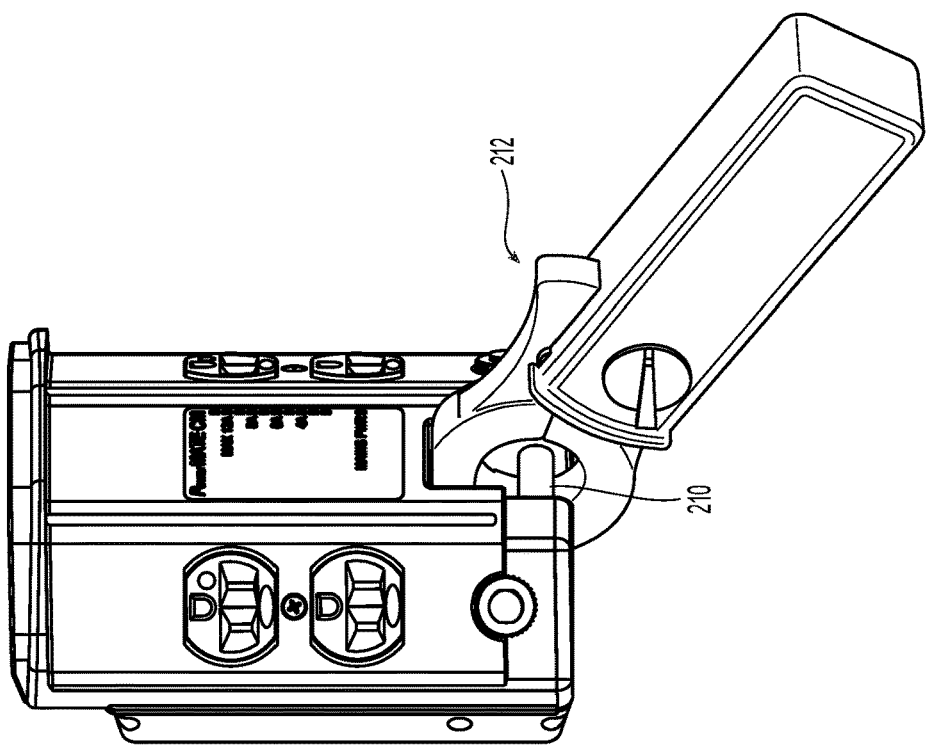
FIG. 14 shows a current probe in the closed positon and mounted on the current bar.
Figure 13:
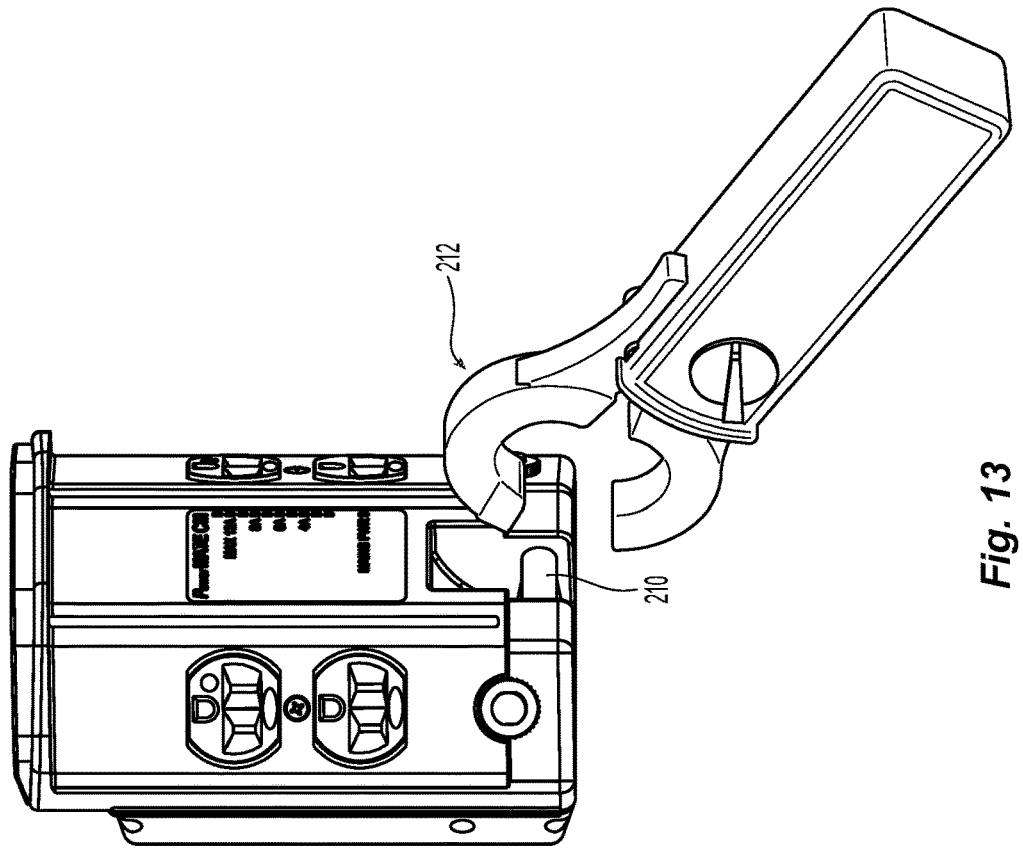
FIG. 13 shows a current probe in the open positon and about to be mounted onto the current bar.

As best seen in FIGS. 13 and 14, the front housing 106 is provided with a current sensor bar 210. The current sensor bar 210 is a hollow passageway formed in the front housing 106. A sensing portion 210a of the electrical circuit passes through the current sensor bar 210. As depicted in FIG. 14, a current clamp probe 212 may be attached around the current sensor bar 210 to directly measure current flow through the SPRPT 100. If desired, a user, inspector or other person may use such a probe 212 to verify that the SPRPT 100 is operating under the maximum allowable current, rather than relying on the current indicator lights 164.

While the present invention has been described herein above in connection with a plurality of aspects and embodiments, it is understood that these aspects and embodiments were presented by way of example with no intention of limiting the invention. Accordingly, the present invention should not be limited to any specific embodiment or aspect, but rather construed in breadth and broad scope in accordance with the recitation of the claims appended hereto.

LIST OF REFERENCE CHARACTERS

100—Relocatable power tap
102—Housing
104—Electrical Cord
105—Plug
106—Front housing
108—Rear housing
110—first facet
112—second facet
114—third facet
120—front housing top
122—front housing bottom
124—top overhang
126—top lip
130—rear housing top
132—rear housing bottom
134—rear channel
135—mounting aperture
136—set screw
137—locking nut
138—clamping surfaces
139—friction pad
140—threaded aperture
142—abutment cap
S1—spacing from topmost receptacle to overhang
150a, 150b—receptacles
154a, 154b, 154c, 154d—sockets
160—display
160a—display panel
160b—amperage indicia
162—mains indicator light
162a—mains display window
164—lighted segments
164a—current display windows
166a—alternative display panel
166b—percentage indicia
168—indicator bar
170a—breaker 1 mounting nut
170b—breaker 2 mounting nut
180a—breaker 1
180b—breaker 2
210—current sensor bar
210a—sensing portion
212—clamp probe
220—mains in
230—current monitor PC Board
232—current transformer
234—low voltage power supply (LVPS)
236—full wave rectifier
238—display circuit
250—filter network
262—voltage divider
270—detection circuit
SIG—Drive signal
400—IV pole
410—pole member
412—IV pole base
414—casters
416—IV pole legs
418—hooks
450—breathing monitor
452—blood pressure monitor
454—heart monitor
456—IV pump
458—IV bags

What is claimed is:

1. A medical electrical equipment relocatable power tap having a power cord with a maximum current rating, comprising:
    a housing having a front side, a rear side, a top side and a bottom side, which together define a housing interior;
    at least four electrical sockets provided on the front side of the housing, each electrical socket configured to receive a plug belonging to an item of medical electrical equipment;
    an electrical circuit mounted in the housing interior, the electrical circuit configured to measure an amount of electrical current being drawn by the power tap; and
    a display provided on the front side of the housing and driven by the electrical circuit, the display configured to provide information reflective of whether the amount of electrical current being drawn by the power tap after an additional item of medical electrical equipment has been plugged into an unoccupied one of the plurality of electrical sockets of the power tap exceeds a maximum allowed current which is less than the maximum current rating of the power cord; wherein:
    the housing further comprises a current sensor bar configured to accommodate an external current probe; and
    the electrical circuit comprises a current monitoring loop which passes through the housing's current sensor bar.

2. The relocatable power tap according to claim 1, wherein:
    the housing's front side comprises first, second and third facets arranged side-by-side with the second facet being located between the first and third facets, each facet extending between the top side and the bottom side;
at least two electrical sockets are provided on each of the first and third facets; and
the display is provided on the second facet.

3. The relocatable power tap according to claim 1, wherein:
the maximum allowed current is a predetermined percentage of the maximum current rating of the power cord.

4. The relocatable power tap according to claim 3, wherein:
the maximum allowed current is 75% of the maximum current rating of the power cord.

5. The relocatable power tap according to claim 4, wherein:
the maximum current rating of the power cord is 20 amps and the maximum allowed current is 15 amps.

6. The relocatable power tap according to claim 3, wherein:
the maximum current rating of the power cord is 16 amps and the maximum allowed current is 12 amps.

7. The relocatable power tap according to claim 1, wherein:
the housing's top side comprises an overhang which overhangs at least the first and third facets; and
the overhang is vertically spaced apart from an uppermost one of the electrical sockets on the first and third facets by a minimum spacing S1>5 cm.

8. The relocatable power tap according to claim 1, wherein:
the electrical sockets belong to hospital grade duplex receptacles;
a total of four electrical sockets are provided; and
the electrical circuit further comprises at least one circuit breaker configured to protect the power tap from excess current draw.

9. The relocatable power tap according to claim 1, wherein:
the display comprises a row of lights configured to function as a bar graph, at least some of the lights differing in color from others of the lights.

10. The relocatable power tap according to claim 1, wherein the electrical circuit comprises:
at least one current sensor configured to sense the instantaneous electrical current flowing through the relocatable power tap, when the relocatable power tap is plugged into an electrical outlet and is used to power at least one item of medical electrical equipment;
a detection circuit configured to measure the instantaneous electrical current, and output a drive signal in response thereto; and
a display circuit configured to control the display, in response to the drive signal.

11. The relocatable power tap according to claim 10, wherein:
the display comprises a row of lights configured to function as a bar graph, the display circuit is configured to illuminate one or more of the lights in response to said drive signal; and
the number of lights illuminated by the display circuit is proportional to a voltage level of the drive signal, and is reflective of the instantaneous electrical current measured.

12. The relocatable power tap according to claim 11, wherein:
the display circuit comprises one or more comparators configured to compare the voltage level of the drive signal with a reference voltage, and
the display circuit is configured to illuminate a particular one of the lights of the row of lights, if the voltage level of the drive signal exceeds the reference voltage.

13. The relocatable power tap according to claim 12, wherein:
the row of lights is a vertical row of lights; and
the display circuit is configured to illuminate the uppermost light in the row of lights, if the voltage level of the drive signal exceeds the reference voltage.

14. The relocatable power tap according to claim 11, wherein:
the display bears indicia reflective of an amperage of the instantaneous current being drawn.

15. The relocatable power tap according to claim 11, wherein:
the display bears indicia reflective of a percentage of the maximum current rating being drawn.

16. The relocatable power tap according to claim 11, wherein:
the display bears indicia in the form of a horizontally oriented indicator bar associated with each current display window, each indicator bar having a different length, the length of a given indicator bar being proportional to the power tap's current draw when its corresponding indicator light is illuminated.

17. The relocatable power tap according to claim 1, further comprising
a channel formed on the housing's rear side and configured to receive a portion of a pole belonging to one or more of an IV pole, a leg or rail of a medical cart, and a leg or rail of a hospital bed;
a clamp assembly comprising a set screw supported by the housing and extending in a first direction transverse to the channel, and at least one clamping surface provided on the housing and facing in a second direction that is opposite to the first direction, wherein:
the set screw and the at least one abutment surface are configured to frictionally mount the housing to the pole, when the power tap is positioned such that a portion of the pole is received into the channel.

18. The relocatable power tap according to claim 17, further comprising
a friction-enhancing pad formed on a wall of the channel, and configured to abut a pole, when the power tap is positioned such that a portion of the pole is received into the channel.

19. The relocatable power tap according to claim 1, further comprising
at least two spaced apart apertures formed on the housing, the apertures configured to receive fasteners for mounting the power tap to a side of a medical cart.

20. The relocatable power tap according to claim 1, wherein:
the top side further comprises an upwardly extending spill lip extending along the overhang, the spill lip configured to prevent liquids from spilling down the facets.

21. The relocatable power tap according to claim 1, further comprising:
an electrical plug via which power is supplied; and
a pair of circuit breakers connected in series with the electrical plug; wherein:

the current monitoring loop includes at least one of said pair of circuit breakers.

* * * * *